(12) United States Patent
Tyrrell

(10) Patent No.: US 6,254,559 B1
(45) Date of Patent: Jul. 3, 2001

(54) ADJUSTABLE HIP JOINT ASSEMBLY

(76) Inventor: Anthony C. Tyrrell, 1861 SW. 55th Ave., Plantation, FL (US) 33317

(*) Notice: Subject to any disclaimer, the term of this patent is extended or adjusted under 35 U.S.C. 154(b) by 0 days.

(21) Appl. No.: 09/384,966

(22) Filed: Aug. 30, 1999

(51) Int. Cl.$^7$ ............................................. A61F 5/00
(52) U.S. Cl. ............................ 602/16; 602/23; 602/24
(58) Field of Search .................... 602/5, 16, 20, 602/23–25, 26, 19; 623/18, 22–23, 27, 39, 47, 53, 57, 59, 61; 403/87, 56, 127

(56) References Cited

U.S. PATENT DOCUMENTS

| | | | |
|---|---|---|---|
| 3,414,908 | * 12/1968 | Waggott | 623/38 |
| 3,671,978 | * 6/1972 | May | 623/18 |
| 4,481,941 | 11/1984 | Rolfes | 128/80 C |
| 4,881,532 | 11/1989 | Borig | 128/80 A |
| 5,344,391 | 9/1994 | Modglin | 602/24 |
| 5,421,810 | * 6/1995 | Davis et al. | 602/16 |
| 5,460,599 | 10/1995 | Davis | 602/16 |
| 5,507,818 | * 4/1996 | McLaughlin | 623/23 |
| 5,669,873 | * 9/1997 | Towsley | 602/16 X |
| 5,766,140 | * 6/1998 | Tillinghast, III | 602/16 |
| 6,027,466 | * 2/2000 | Diefenbacher et al. | 602/16 |
| 6,090,057 | * 7/2000 | Collins et al. | 602/16 |

FOREIGN PATENT DOCUMENTS

| | | | |
|---|---|---|---|
| 2188240 | 10/1987 | (GB) | A61F/5/01 |

\* cited by examiner

Primary Examiner—Denise Pothier
(74) Attorney, Agent, or Firm—Alvin S. Blum

(57) ABSTRACT

An orthopedic hip joint assembly for connection between a pelvis attachment and a thigh attachment is especially useful in stabilizing a patient's hip postoperatively. It provides for free movement in a flexion extension plane between adjustable stops. The flexion extension plane is fixed at an angle to the vertical, preferably at about twenty degrees, so that the leg is neither abducted nor adducted when fully extended for best ambulation. When the leg is flexed for sitting, this angle causes the leg to abduct, or move away from the midline, thus preventing the unstable hip from dislocation or subluxation. A pair of wedge discs are provided, so that the angle between the pelvis attachment and the thigh attachment can be adjusted to fit hips of various widths.

12 Claims, 2 Drawing Sheets

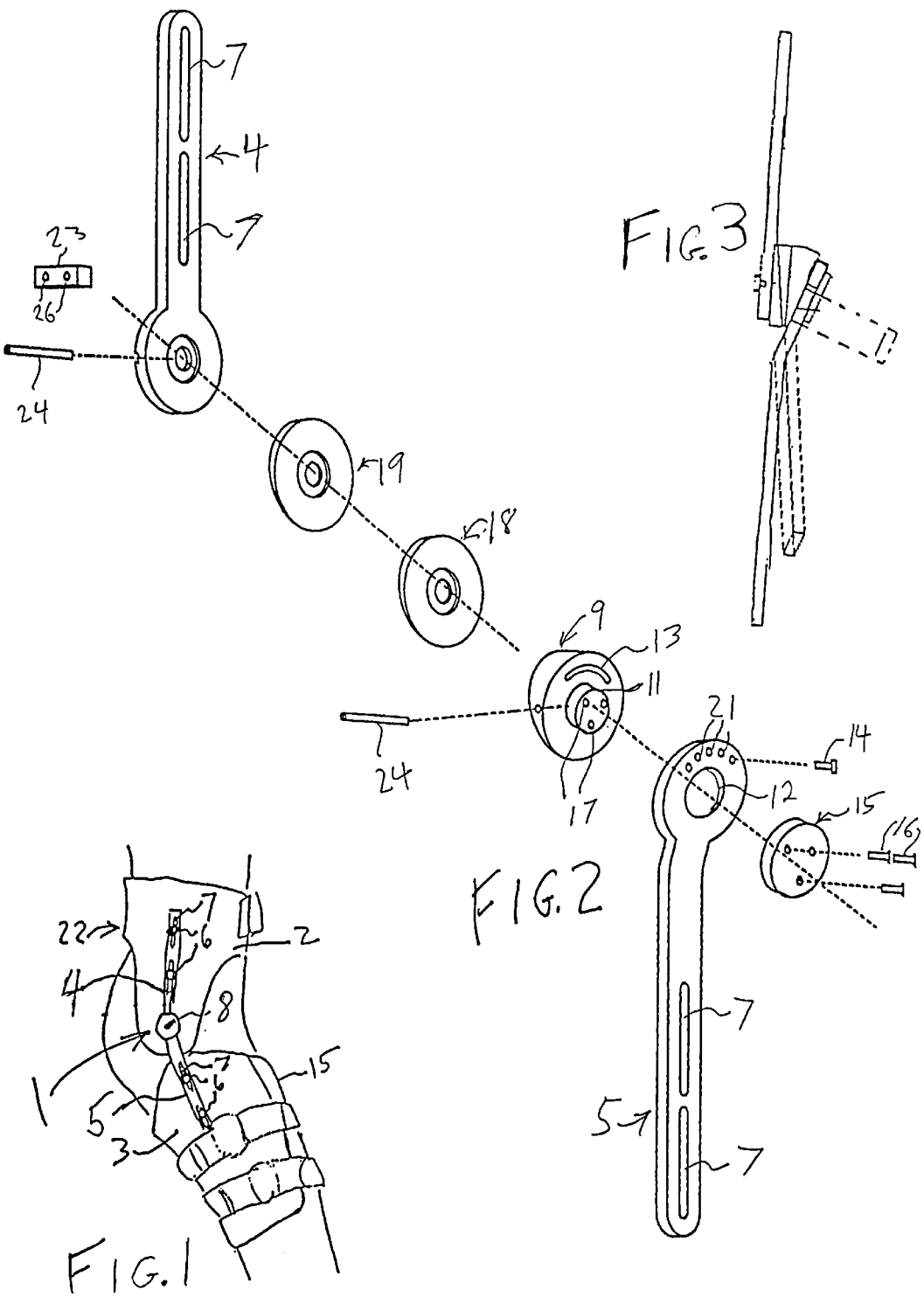

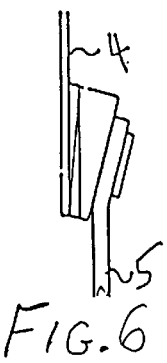
FIG.6
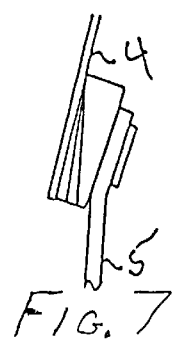
FIG.7
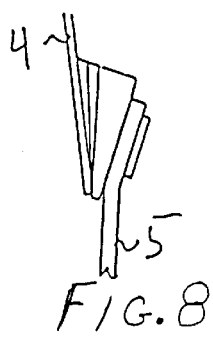
FIG.8
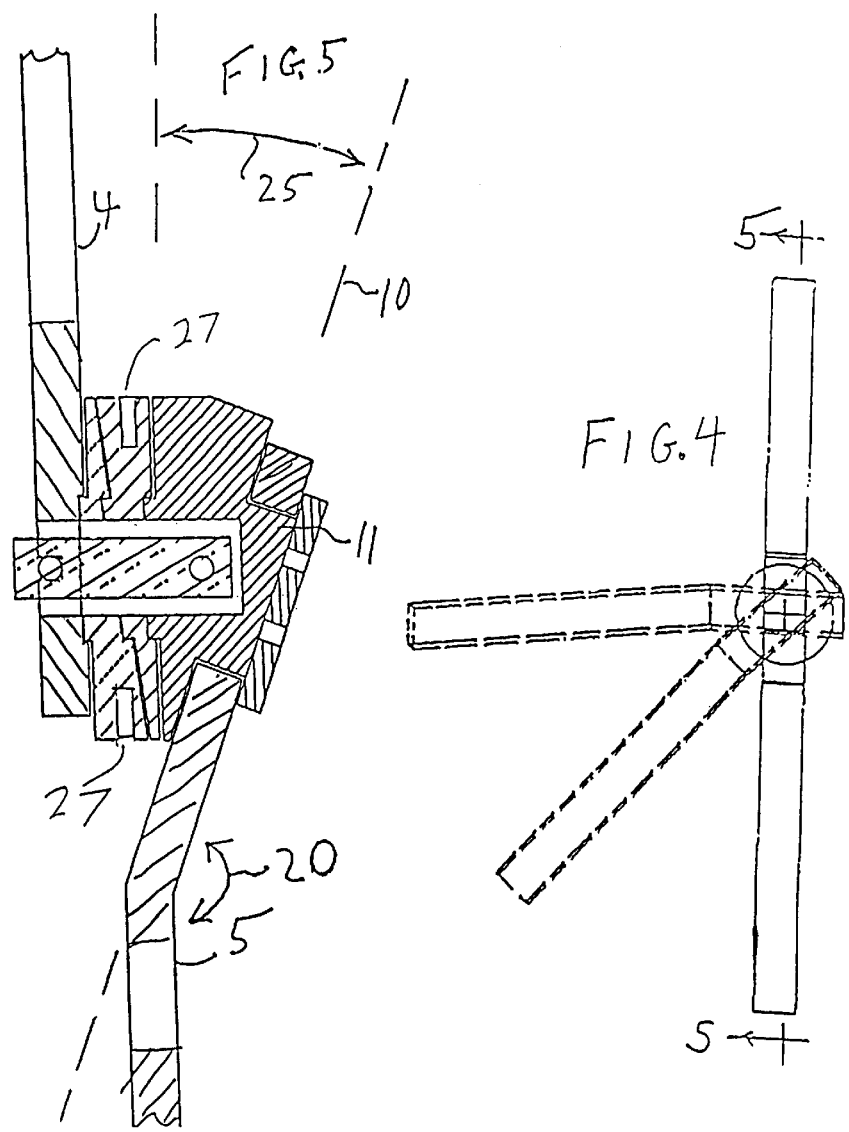
FIG.5
FIG.4

ADJUSTABLE HIP JOINT ASSEMBLY

BACKGROUND OF THE INVENTION

This invention relates to orthopedic devices for limbs and more particularly to a joint assembly for a hip brace that is adjustable to various body shapes while ensuring that the thigh will move from a straight or neutral position wherein extended to an abducted position when flexed to prevent dislocation of the hip joint.

When a hip joint is unstable and subject to subluxation or dislocation, a brace may be employed to stabilize the joint. Such a brace will permit limited movement through the extension/flexion plane while restricting lateral movement i.e. abduction/adduction, or away/toward the midline. Such a brace may be employed for a congenital or injured hip. The most common application of such orthotic devices is after a hip joint has been replaced with an artificial ball and socket joint, especially when the posterior surgical approach is employed. Many of the structures normally holding the ball in place have been cut through. The ball is especially prone to escape from its socket when the leg is flexed and adducted, such as in sitting. To prevent this dislocation, braces applied after hip joint replacement surgery are generally provided with a joint that permits enough flexion extension motion through a limited angle for ambulation and that also provides for a fixed or adjustable degree of abduction. Davis et al. In U.S. Pat. No. 5,421,810 issued Jun. 6, 1995 teach a hinge having a continuously adjustable stop at one end of the extension-flexion rotation. They provide discontinuous means for adjustment of the fixed abduction angle that requires releasing the joint connection, moving the limb to the desired angle, and then tightening the connection. Williamson et al. In U.S. Pat. No 5,368,552 issued Nov. 29, 1994 provide an excellent review of the art and disclose a ball and socket connection in the joint to allow another degree of rotation . Borig et al. In U.S. Pat. No 4,881,532 issued Nov. 21, 1989 disclose ajoint in which there is free abduction through a limited angle.

When fitting a brace, especially a hip brace after surgery, the physician will often prescribe a fixed abduction angle to reduce stress on the joint, especially when sitting. When fabricating the brace, it is difficult to predict what the actual abduction angle will be until it is mounted on the body. If it is not as prescribed, it must be removed, adjusted and mounted again. When the angle is to be changed for some clinical reason, the process must be repeated. When fitting the brace, it is often tempting to disregard small deviations from the required abduction angle. The same holds true for adjustments of the flexion/extension angular extremes.

Diefenbacher and the Applicant, in U.S. patent application Ser. No. 09/148,233 filed Sep. 4, 1998 disclose ajoint with free flexion extension movement between adjustable stops and continuous adjustment of a fixed abduction angle in which the adjustment of abduction angle can be made while the brace is in place on the body.

The joint assemblies of the prior art effectively protect the joint from dislocation when sitting. However, they cause the wearer to stand and walk with the leg abducted. This is uncomfortable and places undue stress on leg structures, and the back. It would be useful to have a brace that would ensure abduction when sitting while providing a leg position when standing and walking that places the foot beneath the hip in a more normal stance.

SUMMARY OF THE INVENTION

It is accordingly an object of the invention to provide an orthotic hip joint brace and hip joint assembly in which the extremes of flexion and extension are adjustable. It is another object that the joint provide a preset angle of abduction when flexed and a substantially neutral or zero degree of abduction when extended. It is yet another object that the invention provide means for adjusting the assembly to fit various body shapes while maintaining these preset flexion/extension and abduction/adduction adjustments.

The hip joint assembly of the invention comprises a first attachment for connection to the pelvis and a second attachment for connection to the thigh of a user. A first elongate connector connects to the first attachment and second elongate connector connects to the second attachment. A pivot support member pivotally supports the second connector for rotary movement through a non vertical plane at a fixed angle of between about ten to thirty degrees, preferably about 20 degrees, from the vertical. Connecting means for connecting the first connector to the pivot support member is adjustable so as to enable the first connector to be aligned with the second connector at maximum extension while the first attachment engages the user's pelvis, the second attachment engages the user's thigh, and the leg is vertical. This structure causes the leg to abduct and rotate externally as it flexes to the sitting position. The leg is substantially vertical during ambulation and abducts substantially when sitting. The first and second attachments are linearly adjustable on their respective connectors so that the rotation point can be adjustably positioned to be precisely lateral to the patient's hip joint . This prevents the attachments from being forced fand down on the body parts during flexion, termed "pistoning" in the art.

These and other objects, features and advantages of the invention will become more apparent when the detailed description is studied in conjunction with the drawings, in which like reference characters indicate like elements in the various drawing figures.

BRIEF DESCRIPTION OF THE DRAWINGS

FIG. 1 is a side elevation view of a hip brace in use that incorporates the joint of the invention.

FIG. 2 is an exploded perspective view of the joint of the invention.

FIG. 3 is a front elevation view of the joint extended to vertical for standing.

FIG. 4 is a side elevation view in the position of FIG. 3.

FIG. 5 is a sectional view taken through line 5—5 of FIG. 4.

FIGS. 6–8 are front detail views showing range of abduction /adduction adjustment.

DETAILED DESCRIPTION OF PREFERRED EMBODIMENTS

Referring now first to FIG. 1, a hip brace 22 of the type used to stabilize the hip, such as after surgical replacement of the natural hip by an artificial hip prosthesis is shown in place on a patient. A padded pelvis first attachment 2 encircles the body securely. A padded thigh second attachment 3 encircles the thigh securely. A joint I of the invention pivotally joins the first and second attachments together to provide mobility to the hip, while restraining movement that might harm the patient such as dislocation of the ball from the socket. First attachment 2 is attached to first elongate connector 4 and second attachment 3 is connected to second elongate connector 5 by removable fasteners 6 that fit into elongate slots 7 in the connectors. The center of rotation 8 of the joint is adjusted to be on the same level as the center of rotation of the hip by loosening fasteners 6 and then sliding the joint up or down until a correct position is found, and then tightening the fasteners. When this adjustment is correct, bending the leg will not tend to raise or lower the attachments. Referring now to FIGS. 2–8, the joint assembly 1 includes an elongate second connector with slots 7 for mounting of the thigh attachment, and a cylindrical aperture 12 that rotatingly receives axle 11 projecting from pivot support member 9. The axle is so positioned that the plane of rotation 10 of connector 5 is at an angle 25 of 20 degrees to the vertical when the bend 20 in connector 5 is also 20 degrees and the brace is adjusted to hold the leg vertical when the wearer is standing. Arcuate slot 13 in member 9 receives one or more angle adjustment pins, or stop elements 14 that pass through selected holes 21 in connector 5 to adjustably limit range of rotary motion of connector 5 about axle 11. Cap plate 15 is fastened to axle 11 by screws 16 in holes 17. First connector 4 is provided with slots 7 for mounting to the pelvis attachment 2 by fasteners 6 to provide for vertical adjustability to a particular patient.

Some patient have wide hips, and other patients have narrow hips. The instant invention provides means for adjusting the joint assembly 1 to ensure that the second connector 5 will be vertical at full extension when mounted on either wide or narrow hips by means of two wedge shaped discs 18, 19 that are rotatably mounted between pivotal support member 9 and first connector 4. These four elements are mounted on square shaft 23 so that they are rotatable relative to one another. Locking pins 24 fit into holes 26 in shaft 23 to hold the four elements together. When the wedge discs 18, 19 are rotated relative to one another, the angle between the first connector 4 and the second connector 5 can be adjusted as shown in FIGS. 6–8 to accommodate the anatomical variations found in clinical practice, while ensuring that the leg will be vertical at full extension. Rotation of discs 18 and 19 are achieved by inserting rods (not shown) into blind holes 27 in the discs and rotating them in opposite directions. They should be rotated through equal angles, so that locking pins 24 can serve as pivots as connectors 4 and 5 change their angular relationship.

The above disclosed invention has a number of particular features which should preferably be employed in combination, although each is useful separately without departure from the scope of the invention. While I have shown and described the preferred embodiments of my invention, it will be understood that the invention may be embodied otherwise than herein specifically illustrated or described, and that certain changes in form and arrangement of parts and the specific manner of practicing the invention may be made within the underlying idea or principles of the invention.

What is claimed is:

1. An external orthopedic joint for connection between a first attachment for encircling a pelvis and a second attachment for encircling a thigh, the external joint comprising:
   a first elongate connector adapted for attaching to said first attachment;
   a second elongate connector adapted for attaching to said second attachment;
   a pivotal support member pivotally supporting the second connector for rotary movement of the second connector through a non vertical plane; and adjustable connecting means for adjustably connecting the first connector to the pivotal support member such that the angle of the vertical plane of rotary movement relative to a vertical plane may be adjusted while the first attachment encircles the pelvis and the second attachment encircles the thigh and the leg is vertical, to thereby cause the leg to abduct by a presettable amount when flexed to a sitting position while maintaining a substantially vertical position of the leg when extended for standing and ambulation.

2. The joint according to claim 1, in which the first and second elongate connectors each have a long axis and means are provided for adjustably connecting the first and second attachments thereto at selected points along the long axes so as to adjustably position the pivotal support member to be laterally adjacent the hip joint of the user.

3. The joint according to claim 2, further comprising stop elements for adjustably limiting range of pivotal motion about the pivot support member.

4. The joint according to claim 3, wherein said connecting means comprises paired coaxial wedge elements interposed between the pivotal support member and the first connector for adjusting angular relationship between the first and second connectors to thereby accommodate diverse body shapes while maintaining the second connector vertical at full extension.

5. The joint according to claim 4, in which said non vertical plane is at an angle of about twenty degrees from the vertical plane.

6. The joint according to claim 4, in which said non vertical plane is at an angle of between about ten to thirty degrees from the vertical plane.

7. The joint according to claim 1, in which said non vertical plane is at an angle of about twenty degrees from the vertical plane.

8. The joint according to claim 1, in which said non vertical plane is at an angle of between about ten to thirty degrees from the vertical plane.

9. An external orthopedic joint for connection between a first attachment for encircling pelvis and a second attachment for encircling a thigh, the external joint comprising:
   a first connector adapted for attaching to said first attachment;
   a second connector adapted for attaching to said second attachment;
   a pivotal support member pivotally supporting the second connector for rotary movement of the second connector through a plane at a fixed angle of about twenty degrees from a vertical plane; and
   adjustable connecting means for adjustably connecting the first connector to the pivotal support member for adjusting the angle of the plane of rotary movement while the first attachment encircles the pelvis and the second attachment encircles the thigh and the leg is vertical, to thereby cause the leg to abduct by a presettable amount when flexed to a sitting position while maintaining a substantially vertical position when extended for standing and ambulation.

10. An external orthopedic joint for connection between a first attachment for encircling a pelvis and a second attachment for encircling a thigh, the external joint comprising:
   a first elongate connector adapted for attaching to said first attachment;
   a second elongate connector adapted for attaching to said second attachment;
   a pivotal support member pivotally supporting the second connector for rotary movement of the second connector through a non vertical plane;
   adjustable connecting means for adjustably connecting the first connector to the pivotal support member for adjusting the angle of the non vertical plane of rotary movement while the first attachment encircles the pelvis and the second attachment encircles the thigh and the leg is vertical, to thereby cause the leg to abduct when flexed to a sitting position while maintaining a substantially vertical position when extended for standing and ambulation;

in which the first and second elongate connectors each have a long axis and means are provided for adjustably connecting the first and second attachments thereto at selected points along the long axes so as to adjustably position the pivotal support member to be laterally adjacent the hip joint of the user;

stop elements for adjustably limiting range of pivotal motion about the pivot support member; and said connecting means comprising paired coaxial wedge elements interposed between the pivotal support member and the first connector for adjusting angular relationship between the first and second connectors to thereby accommodate diverse body shapes while maintaining the second connector vertical at full extension.

11. The joint according to claim 10, in which said non vertical plane is at an angle of about twenty degrees from a vertical plane.

12. The joint according to claim 10, in which said non vertical plane is at an angle of between about ten to thirty degrees from a vertical plane.

* * * * *